(12) United States Patent
Blumenthal (10) Patent No.: US 6,565,504 B2
(45) Date of Patent: May 20, 2003

(54) METHOD AND APPARATUS TO CREATE AND INDUCE A SELF-CREATED HYPNOSIS

(76) Inventor: Richard A. Blumenthal, 111 Beach Rd., Westhampton Beach, NY (US) 11978

( * ) Notice: Subject to any disclaimer, the term of this patent is extended or adjusted under 35 U.S.C. 154(b) by 0 days.

(21) Appl. No.: 09/769,651

(22) Filed: Jan. 25, 2001

(65) Prior Publication Data

US 2001/0005770 A1 Jun. 28, 2001

Related U.S. Application Data (63) Continuation-in-part of application No. 09/139,098, filed on Aug. 24, 1998, now abandoned.

(51) Int. Cl.[7] .................. A61M 21/00; G09B 19/00; G06T 15/00; A61B 5/04
(52) U.S. Cl. .................. 600/26; 434/238; 345/418; 600/545
(58) Field of Search .................. 345/419; 434/236; 128/898; 600/26, 545, 547

(56) References Cited

U.S. PATENT DOCUMENTS

| | | | | |
|---|---|---|---|---|
| 3,691,652 A | * | 9/1972 | Clynes | 434/236 |
| 5,425,699 A | * | 6/1995 | Speigel | 128/898 |
| 5,722,418 A | * | 3/1998 | Bro | 600/545 |
| 5,736,986 A | * | 4/1998 | Sever, Jr. | 345/419 |
| 5,823,932 A | * | 10/1998 | Speigel | 600/26 |
| 6,026,322 A | * | 2/2000 | Korenman et al. | 600/547 |
| 6,057,846 A | * | 5/2000 | Sever, Jr. | 345/419 |
| 6,258,022 B1 | * | 7/2001 | Rose | 600/26 |

* cited by examiner

Primary Examiner—Eric F. Winakur
Assistant Examiner—Nikita R Veniaminov
(74) Attorney, Agent, or Firm—Kelly & Hulme, P.C.

(57) ABSTRACT

This invention provides a method and apparatus operable within an interactive computer device for presentation to the visual and auditory senses. The invention uses the creation and use of a custom hypnosis script to induce a state of hypnosis and make behavioral suggestions, Through questions presented, the user is queried for the user's preferences for hypnotic induction imagery and behavioral suggestion. The user enters the preferences, employing a keyboard, and/or a mouse, and/or other such device used to enter information. The program inserts the user responses into a preprogrammed textual material to compile a complete hypnosis script. A text-to-speech component of the program enables the user to then listen to the custom hypnosis script, and thereby experience a complete, custom hypnosis.

3 Claims, 4 Drawing Sheets

Custom Topic – Feelings

Once you are relaxed and involved in your imagination, you will be open to new ideas that will help you to feel, do and be more the way you want. Please enter your answers to the questions that apply to you.

Is there a feeling you wish to change? Please complete this sentence. I want to change feeling.

[                                              ] Play

How do you want to feel instead? Please complete this sentence. I want to feel.

[                                              ] Play

What idea or ideas might help you to feel the way you want? Please complete these sentences. I want to think.

[                                              ] Play

I want to think.

[                                              ] Play

Use the Tab key to move to the next section.

| Change Voice | Save | Topics Tips | Language Tips | Back | Next | Cancel |

FIG.3

Topic Choices

Once you are relaxed and involved in your imagination, you will be open to new ideas that will help you feel, do and be more the way you want. Please select as many of the topics listed below that you would like to include. Each one has some wonderful ideas which will automatically become part of your hypnosis.

| | | |
|---|---|---|
| ☒ Smoking Control | ☐ After Surgery | ☐ Controlling Shopping |
| ☐ Weight Control | ☐ Increasing Self-Esteem | ☐ Credit Card Wisdom |
| ☐ Stress Management | ☐ Enjoying Life | ☐ Controlling Hyperactive Behavior |
| ☐ Pain Management | ☐ Resisting Substance Abuse | ☐ Exercising Regularly |
| ☐ Encourage Healing | ☐ Job Performance | ☐ Gambling Control |
| ☐ Enhancing Attractiveness | ☐ Improving Memory | ☐ Comfortable Flying |
| ☐ Restful Sleep | ☐ Test Performance | ☐ Body Image, Body Shaping |
| ☐ Dealing With Loss | ☐ Enhancing Assertiveness | ☐ Being On Time |
| ☐ Anxiety Control | ☐ Sports Performance | ☐ Post Traumatic Stress |
| ☐ Before Surgery | ☐ Dealing With Difficult People | ☐ Controlling Obsessive/Compulsive Tendencies |

Modify Topic Text

☒ Custom

Create custom topics...

Change Voice | Save | Topics Tips | Language Tips | Back | Next | Cancel

FIG.4

METHOD AND APPARATUS TO CREATE AND INDUCE A SELF-CREATED HYPNOSIS

This application is a continuation-in-part of U.S. Ser. No. 09/139,048 filed Aug. 24, 1998, abandoned Jan. 27, 2001.

BACKGROUND OF THE INVENTION

1. Field of Invention

The instant invention relates to a method and apparatus for the purpose of self-creating and using a custom hypnosis script that may be used to induce a hypnotic state in a user. In particular this invention relates to the use of a computer program for use with a computer, which queries a user and guides such user through the steps necessary for the creation of a hypnosis script including the imagery to produce hypnotic induction and the behavioral suggestions to produce a desired post-hypnotic effect. Through the use of a text-to-speech program component, the user is able to listen to the completed hypnosis script and thus benefit from a custom created hypnosis experience.

2. Description of Prior Art

A hypnotic state has been described as an altered state of consciousness with an associated heightened level of suggestibility. This heightened level of suggestibility has been found useful in the field for helping to treat people with a wide range of problems or issues relative to weight loss, addiction, pain management, time management and many other areas.

Useful techniques for inducing such an hypnotic state generally fall into three categories: drug induced hypnosis, concentration induced hypnosis (i.e., the swinging watch) and imagery. Of the three categories imagery is believed to be the most useful as it produced a useful hypnotic state (with the associated heightened level of suggestibility) without the stress of concentration (which also produces an unrelaxed state) or the side effects of drug induced states. In addition, the imagery method can be employed at almost any location without the need for unusual equipment or medical oversight.

In light of the benefits of an imagery induced hypnotic state, the market place has produced a plethora of imagery based techniques of providing the desired hypnotic state. For many years, these mass-produced hypnosis products have utilized a spoken hypnosis script which includes the working of hypnotic induction imagery, as well as the working of hypnotic behavioral suggestions. One form of these products offer the user either an audio or a video version of a predetermined hypnosis script, but are not intended for custom alteration by the user. The user of these products must conform to the imagery and suggestion choices as presented, even if some or all of it fails to suit the user's precise needs and/or preferences.

Another product is the virtual reality device which provides presentation to at least the visual senses, but making no specific mention of the spoken word. Furthermore, it provides that special gear must be worn by the user to produce an actual, not imagery, visual presentation of the experience. The device and its associated accessories do not create or utilize a hypnosis script including neither hypnotic induction language meant to stimulate the imagination of the user, nor hypnotic behavioral suggestion language meant to produce a post-hypnotic effect.

It is, therefore, an object of the present invention to provide a method and associated apparatus for inducing a hypnotic state in a user.

It is another objective of the present invention to provide a method and associated apparatus that creates such an hypnotic state through the use of a self-created hypnotic script.

It is yet another objective of the present invention to provide a method and apparatus wherein said hypnotic script is spoken aloud and which script may be customized by the user.

These and other objectives of the present invention shall become apparent from the following specification, read in conjunction with the appended claims and attached drawings.

SUMMARY OF THE INVENTION

The apparatus taught by the present invention comprises a medium with a computer program imprinted thereon, operable within an interactive computer device equipped with means to present to the visual and auditory senses and further equipped with means to receive user input. The computer program provides the user with a method for creating and listening to a custom hypnosis script for the purpose of inducing a state of hypnosis and making hypnotic behavioral suggestions. The term custom refers to the inclusion of user selected preferences for the imagery and behavioral suggestions in the hypnosis script.

The method advantageously using this apparatus is comprised of operatively interfacing the program medium with the computer device; running the program, such that the program through the use of predetermined queries solicits input from the user which input is then incorporated into an hypnotic script provided by the program; and presenting the hypnotic script to the user.

BRIEF DESCRIPTION OF THE DRAWINGS

FIG. 4 is yet another example of an additional visual query display typical of the present invention.

DETAILED DESCRIPTION OF THE INVENTION

With reference to the drawings, there is depicted and described an apparatus and a method employing such apparatus for preparing and presenting a user customized hypnotic script which script when present to a user will produce an hypnotic state with an elevated level of suggestibility. The heightened level allows the user to be receptive to the imagery and behavioral suggestions that are made through the hypnotic script.

In order to obtain the advantages of the present invention, a typical interactive computer with a key board, mouse or other input means is provided which computer is also provided with text to speech attributes. Provided within the computer and on any typically provided storage media (a hard drive, floppy disc or the like) is a computer program which program is designed to query a user to provide certain information via the computer input means so that a self created, customized hypnotic script may be created.

Figure 1:
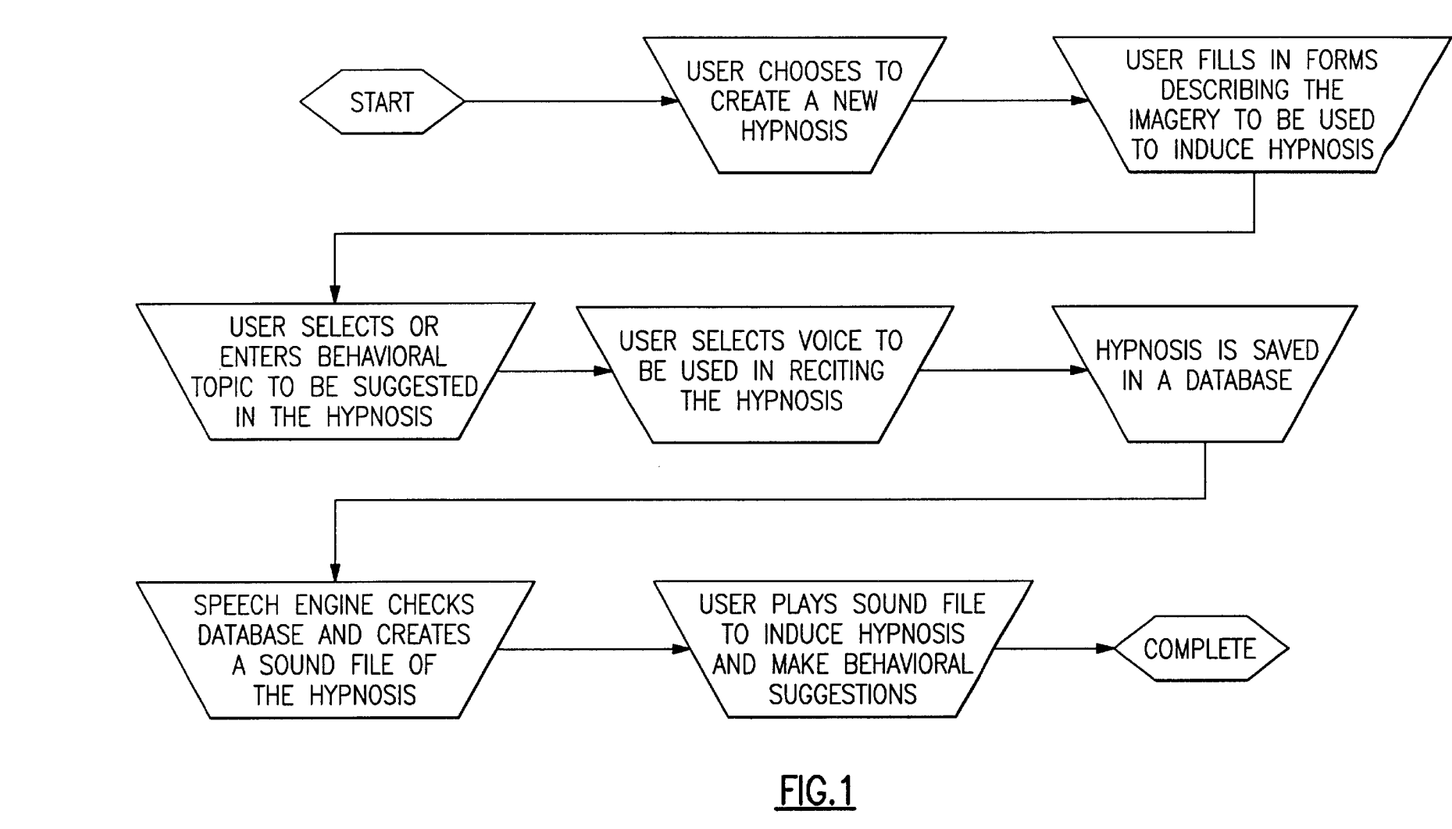
FIG. 1 is a flow chart describing the function of the computer program advantageously employed in the present invention.

The logical flow chart of the program itself is described in FIG. 1 which is a flow chart of the steps the program is required to perform in accordance with the present invention. As can be seen from FIG. 1, the program provides a customizable hypnotic script. This script can take any form suitable for the task at hand and prepared in accordance with standard hypnotic guidelines. A typical script found useful in accordance with the present invention is shown in Example 1 below.

As can be seen in Example 1, the script has a series of user defined, user entered information identified throughout the Example 1 as a "(User Entered Information)". As described in more details below the program queries the user to provide imagery words to insert into these user defined fields.

As can also be seen in Example 1, the script may also incorporate certain behavioral suggestions. While these suggestions may take any useful form a series of such suggestions are provided in Example 2 below. As will also be described in more detail below, the inclusion of such behavioral suggestions results from a query of the user by the computer program and selection by the user.

Figure 2:
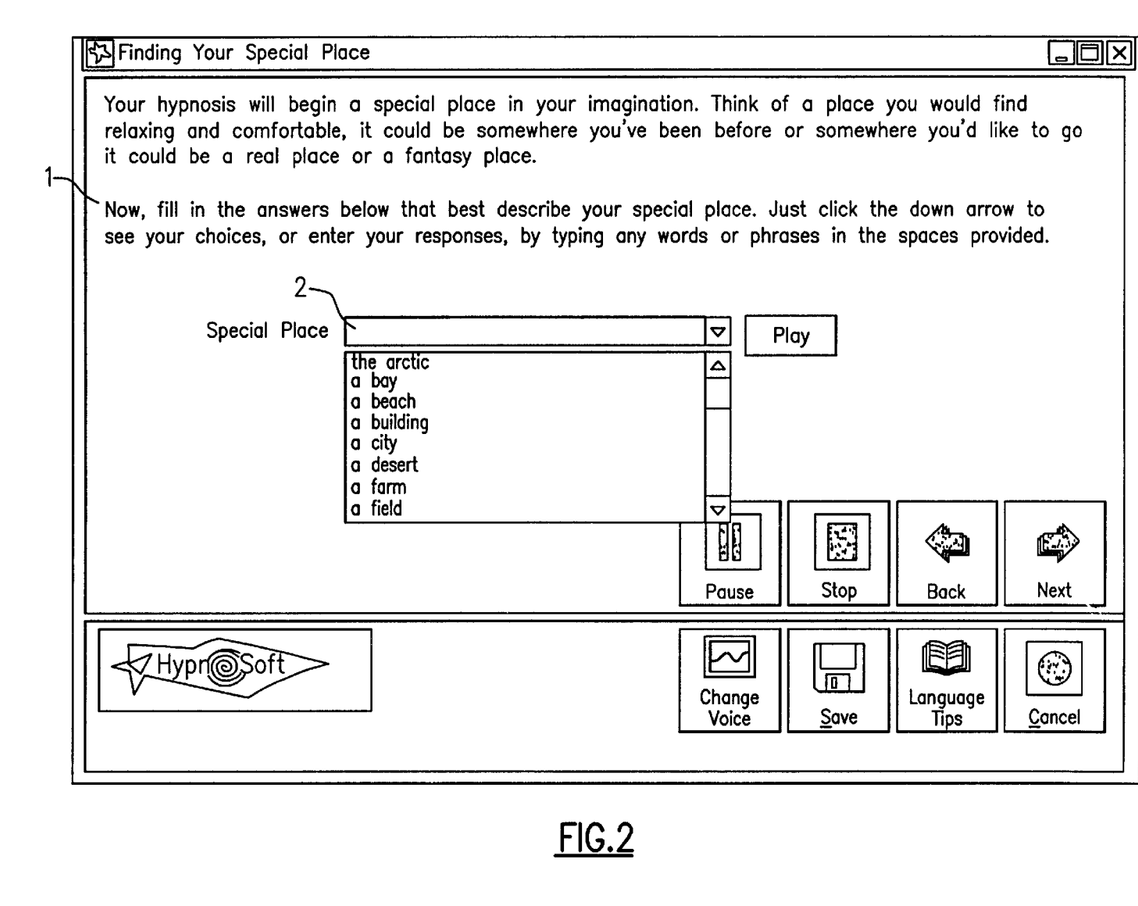
FIG. 2 is an example of a visual query display typical of the present invention.
Figure 3:
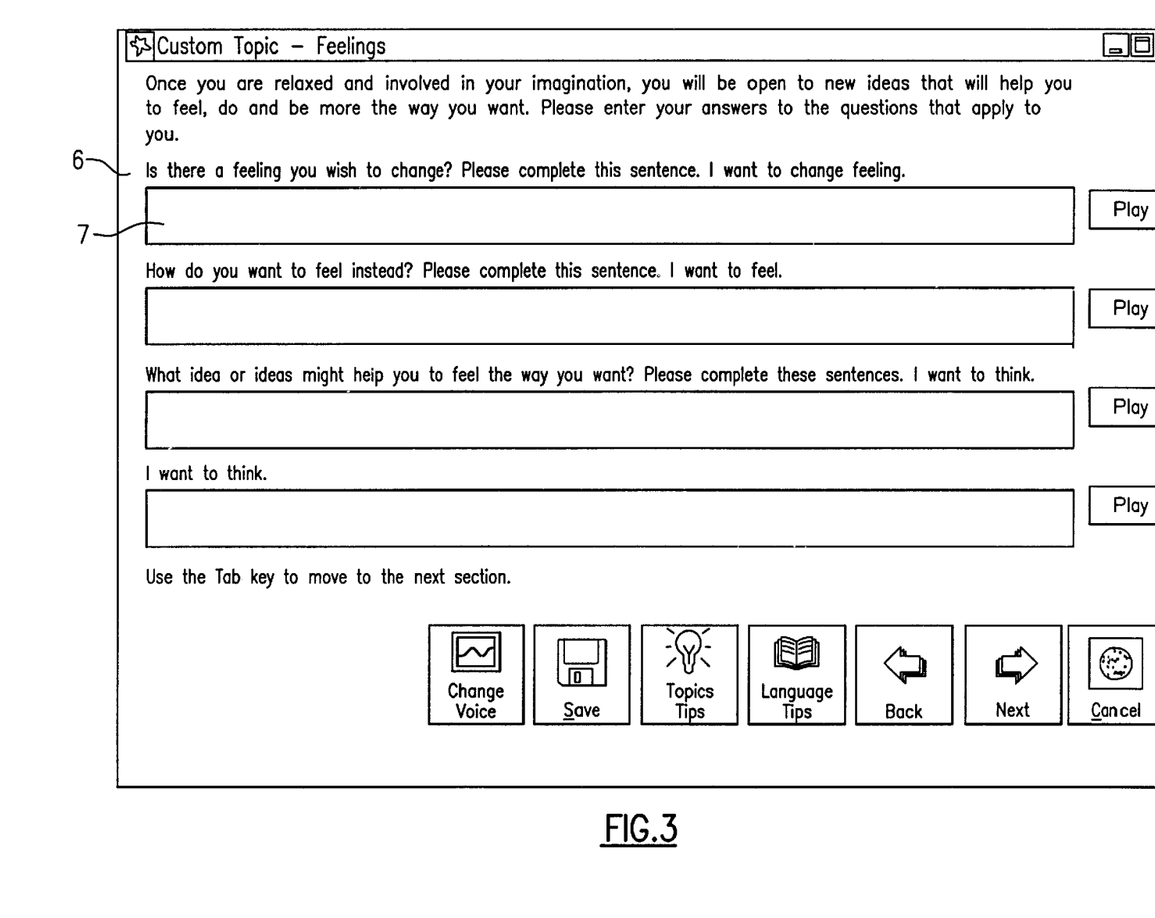
FIG. 3 is an example of additional visual query display typical of the present invention.

Depicted in FIGS. 2 and 3 are computer displays typical of those created by the computer program of the present invention; FIG. 1 querying the user as to the imagery of the script and FIG. 2 querying the user as to any behavior suggestions the user may wish to incorporate into the hypnotic script.

As can be seen by a review of the hypnotic script, the user will choose hypnosis scripting preferences for the wording of hypnosis induction imagery, by answering questions about the desired imagery regarding the setting, the sights, the sounds, the smells, the colors, the season, the temperature, the user's physical presence and/or other such descriptive terms as may be included in the hypnosis imagery. These preferences are typically entered into the program by means of a keyboard, and/or a mouse, and/or any other known device which may be used for entering such information.

As described above, the program also presents a visual display (an example is depicted in FIG. 3), which prompts the computer user to enter a selection regarding the behavioral suggestion topic the user wishes to address in the hypnosis script, such as stop smoking, encourage healing, enjoying life, controlling anxiety and/or other such behavior. The topic selection is associated with appropriate preprogrammed text which is then included in the hypnosis script.

The user may also offer the option of creating a wholly original behavioral suggestion. If this option is selected, the program presents visual displays, an example is depicted in FIG. 4, which prompt the user to enter preferences regarding the precise wording of hypnosis suggestions. The user's responses are entered into the program by means of a keyboard, and/or a mouse, and/or any other known device for entering information.

As the user enters any of the imagery or behavioral preferences, the program automatically inserts them into appropriate points of the hypnosis script text, sufficient to link all the user preferences together and form a meaningful, effective hypnosis script.

Returning to FIG. 1, after the user has completely responded to the queries of the program, the user selects the form of audio voice in which the script will be recited, the script is then saved in the form of a computer file and converted into a sound file which file can then be played and replayed by the user over the audio function of the apparatus used in accordance with the present invention. It is the playing of the script and the user's attention to the playing of the script which produces the advantageous hypnotic effect of the present invention.

The script once played may be stored or saved as typically done with current computer technology. The script can then be played and replayed by the user as desired. The user may also return at any time to the program and create a new script.

As described above, the hypnotic script is played through the sound or audio system of a typical computer and takes the form of an electrically reproduced soothing "voice" which "voice" recites the script to the user. In addition to the voice, the script may also include other reproduced sounds such as music, sounds of nature and the like.

The computer program used to generate the hypnotic script may be operated and interacted with in any manner known in the art, including operation on a standard desk top or lap top computer or remotely via the Internet with the user interacting with said program by contacting a web site and with the user customized hypnotic script being "e-mailed" to the user for playing. In any such case a typical user interacts with the program by responding (typically with a computer keyboard) to queries generated by the program with the program consolidating these responses into a hypnotic script.

EXAMPLE 1

Sample Hypnosis Script

At any time, during this hypnosis, you are fully able to awaken yourself, and return to your ordinary thinking. Uncross the legs, and arms. Tell your hands and face to relax. Let all your muscles. and bones, relax. Your whole body from your feet to your scalp are allowed to relax. Give yourself complete permission, to take a break from your ordinary thinking and simply be comfortable. Give this to yourself, as a welcome gift.

Now, you become aware of your breathing. You breathe normally, and easily. Each time you inhale you breathe in, relaxation and comfort. Each time you exhale you breathe out tensions, and worries and they dissipate, far away from you. You inhale and breathe in relaxation and comfort. You exhale and breathe out tensions and worries. Breathe in relaxation. Breathe out tension. Breathe in relaxation. Breathe out tension. You feel good and comfortable.

In your imagination you can picture yourself, in a wonderful place (User Entered Information). This is a place, created just for you. A place for you to be, relaxed, and comfortable. You feel good as you (User Entered Information) in this special place. It is (User Entered Information) and it is (User Entered Information) here. It is (User Entered Information). It is (User Entered Information). As you look around, you can see (User Entered Information), (User Entered Information), and (User Entered Information). You see (User Entered Information)i (User Entered Information), and (User Entered Information). It feels (User Entered Information), in this special place. You can smell (User Entered Information), here. You hear (User Entered Information). You feel so comfortable and good, in this wonderful place. You enjoy just being here.

In the distance, a little way from where you are, you notice a small cottage. It would take you twenty steps to reach the door of the cottage. You know that in this cottage you will certainly be able to obtain excellent ideas, that will help you to be, who you want to be, and feel what you want to feel.

You decide that you definitely want to walk the twenty steps to the door of the cottage. You begin. Take the first step. Take the second step. Take the third step, feeling very good. Take the fourth step. Take the fifth step. Take the sixth step, feeling very safe. Take the seventh step. Take the eighth step. Take the ninth step. Take the tenth step. Take the eleventh step. Take the twelfth step. Take the thirteenth step. Take the fourteenth step. Take the fifteenth step. Take the sixteenth step. Take the seventeenth step. Take the eighteenth step. Take the nineteenth step. And take the twentieth step.

You stand at the door of the cottage. Now open the door. Step inside. You find yourself, in a beautiful room. The room, is decorated just the way you like. You see all of the colors you like and as you look around, you see the beautiful things in this room. You feel wonderful, just being here. You feel safe and peaceful. This is a place, created just for you, for you to feel good, and relaxed.

In the corner of the room, you see a comfortable chair. You move to the chair. You sit down, finding it extremely comfortable and soothing. As you sit there, you begin to think about how you can help yourself to become the person you truly wish to be. You think about yourself and how much you wish you could change certain things about you. You realize that you have tremendous power to make the changes you wish for.

(This part of the script consists of either a user-selected, preprogrammed behavioral suggestion or, if optionally created by the user, the following dialogue)

You think about (User Entered Information). You decide, with strength and confidence to transform this into (User Entered Information). You fully understand, believe, and totally accept (User Entered Information). You fully understand, believe, and totally accept (User Entered Information).

You can feel the immense healing power you have unleashed. You can see and experience it, helping you to be healthy. You allow these powerful and positive ideas to enter the deepest parts of your mind and body, filling you with a strength that causes you to be who you want to be. The person you have now become and from now on, is able to attain the goals you have set forth for yourself, with confidence creating for yourself a wonderful life!

Now rest and enjoy all you have accomplished. You can return to this special place whenever you wish to reinforce good ideas, to give yourself new ideas, or simply to relax. A good way of reinforcing the ideas you need, even when you haven't much time, is to say,(User Entered Information) to yourself. This will help you without having to go into your deep relaxation.

In a moment, you will hear a count of three, moving backward, from three to one. When you reach one, you will awaken, feeling refreshed and comfortable. Three, two, one. You are awake.

We hope you enjoyed your hypnosis.

EXAMPLE 2

Sample Preprogrammed Behavioral Suggestions
Weight Control
I choose to eat healthy, good foods in portions I know are right for me. I will eat and exercise properly and wisely, so that I can attain the weight that is healthiest for me. I do all of this to love and care for myself. I call on my inner strength to make this wise decision and take control of the way I wish to live, from now on. I choose a healthy, happy lifestyle.

Smoking Control
I fully understand that smoking poisons my body and shortens my life. I want to enjoy good health and long life. I completely reject the poison of smoking. The smoker phase of my life is over. A wonderfully, healthy phase has begun. I feel the goodness of this decision already. Each moment brings greater and greater conviction and resolve to live my life as a non-smoker. This feels strong and good to me. I am proud and happy with this wonderful decision I have made.

Pain Management
I am aware that there is some pain in my body. However, as each moment passes I feel more and more comfortable, more and more at ease. The pain can now be put in a distant place and I am able to control how much attention I wish to pay it. With this power, I choose to focus my attention on other, more pleasant things.

Stress Management
Life can sometimes become complicated. It is not always possible to have all of the answers, all the time. I, therefore, feel satisfied that I have only partial answers sometimes. In fact, there may be no answer to a difficult question. I know that no human being is perfect, including me. Though I am a capable, competent person, I fully accept that I cannot expect total perfection from myself and I completely forgive myself for being less than absolutely perfect. Even in the face of great pressure, I know that I am at peace with myself, inside.

Anxiety Control
I know that sometimes I have felt anxious in the past. I have decided that this feeling will become more and more unusual in my life. However, if I should feel anxious or fearful, I am certain that the unpleasantness will pass quickly and I will be fine. I will live through the experience and I will be okay in just a few minutes. Knowing this feels good and strong. I feel powerful and confident that I will be able to cope, even if the situation seems difficult at first. I can and I will cope.

Increasing Self-Esteem
I can see myself as the person I truly want to be as though I were looking into a wonderful mirror. I can see the confident expression on my face, the sure way I am standing, the self-assured clothing I am wearing and I now direct that energy to heal my body. Every part of my body is to be healed, from the largest organ to the smallest cell. I will fully cooperate in my healing process; moving ever forward to a complete healing and total recovery. My body has received the instructions to mend and I can feel the process taking place already. I am well on my way to a wonderful recovery.

Restful Sleep
I am able to choose the proper time for me to sleep. When that time arrives, I will easily relax, be comfortable and gently drift off into a sound sleep. I will sleep well, enjoying a revitalizing, restful sleep. I will awaken at the right moment, feeling well-rested and refreshed.

Test Performance
Whenever I am tested, whether I have known a test is coming or I am surprised by a test, I will perform at my very best. I will call on my total memory and find all of the information and understanding required. I will be relaxed, yet alert and completely focused my energy on the question at hand, using my time wisely and successfully.

Enjoying Life
Whatever happened to me before, whatever I have done before, I know, in my heart that I deserve to be happy and enjoy good feelings. I deserve to enjoy my life, appreciating and enjoying the simple, everyday things, as well as the special occasions. I give myself permission to enjoy the smell and taste of food, to enjoy laughing at something funny, to enjoy seeing and listening to beauty. I give myself permission to enjoy the people I love. I allow myself to smile often and to feel good that I am alive. Even if something I don't like happens and I cannot control it, I still can accept the bad with the good and be thankful for having a variety of emotions. Usually, I will be able to find reasons to be happy, because this is what I truly deserve.

Job Performance

I will bring forward my energy and intelligence to do excellent work that I am proud to present. I am relaxed, but alert and insightful. No matter what task is given me, I will do my utmost to complete it with competence and skill. To do this, I draw on my superior talents and skills, working effectively with other people whenever necessary and doing the best job I am capable of doing. I feel satisfied that I am a capable, competent person.

Dealing With Difficult People and Situations

I understand and accept that life may present people and situations that are difficult and distasteful. Though I would prefer to deal only with nice people and pleasant situations, this is not always possible because I sometimes there are great benefits to me as a result of dealing with difficulty. I sometimes must put my own long range interests above the unpleasantness in order to successfully deal with it. I am actually able to focus on what I need from the person or situation and feel good that I am moving to making important gains. With this understanding, I feel relaxed and good about myself.

Sports Performance

Whenever I participate in a sporting contest or sporting event of my choosing, I will purposefully instruct my body and mind to act together to use my strength and concentration for performing my very best. I definitely choose to accomplish the most perfect performance of which I am capable. I feel powerful and confident in my talent and ability.

Improving Memory

I possess great mental energy. I am able to direct this energy as I please. When I choose, I can direct my great mental energy to my memory. My memory is precise and complete. When I try, I am able to remember experiences I have had and information I need I in detail. When I study a particular subject or whenever else I wish, I will open my mind to capture information and easily be able to recall it at will. My memory grows stronger.

Resisting Substance Abuse

Whenever I need to, I am able to find and use a great power to make good, lasting choices. Therefore, if I happen to feel a desire to use a particular substance that I want to avoid, I will look for, find and use the power to make good choices. I will allow the desire to pass harmlessly. I understand that this feeling of desiring the substance could happen again, but I also know that the good power grows stronger and stronger within me. I can certainly make good and lasting choices whenever I have the need to do so.

Enhance Attractiveness

I feel myself becoming the person I want to be. I am comfortable and actually enjoy being around people. When I am with other people, my thoughts flow easily and I am able to speak with ease, as Well, knowing that I am worth at least as much as any other person on the planet. My manner is relaxed and self-assured. When it is appropriate, I smile with grace and charm, knowing that I am attractive. Other people enjoy being with me and I enjoy their company, too. I will certainly attract friends and lovers if I should desire.

Enhance Assertiveness

I feel myself becoming the person I want to be. I am a capable, intelligent person with a lot of good sense. I am confident that my decision-making is strong and that my ideas have merit. I weigh my decisions carefully and have the power to change my mind, but only when I am thoroughly convinced. I know that my opinions are worth at least as much as anyone else's. I am able to speak my mind and ask for what I want with strength and clarity. I refuse to tolerate other people imposing their ideas on me, unless, for my own reasons I choose to go along willingly.

Before Surgery

I know that I will soon go through surgery. I want this to be a wonderful success. I, therefore, direct my mind and body to completely cooperate with my Doctors and others who will participate in this experience. I will follow their instructions to the very best of my ability. I have faith in my Doctor's expertise and in my eventual, full recovery. I am comfortable and absolutely certain that everything will go extremely well.

After Surgery

I fully expect a complete recovery from the surgery I have gone through. I will do everything I possibly can to cooperate with my Doctors and others who will participate in this experience. I direct my mind and body to heal and become strong. I can and will focus my tremendous power and energy on accomplishing my total recovery. The healing has already begun and I can feel it growing even now. I have great hopes for my wonderful future.

Dealing With Loss

I know that I have gone through a great loss. This has been a difficult and trying experience. I have mourned and will continue to mourn my loss because I am a feeling human being. I also know that I have wonderful things ahead of me and that my life still holds great promise. Though I will always cherish my memories and feel my loss, I also cherish my life and feel my hope. I know that I am able to summon my strength from within and help myself cope with my day to day living. As time goes on I will feel more and more my confident, true self. I have many good things ahead of me. My memories bring me love and wisdom.

Controlling Shopping

I now decide that shopping is an important activity to be treated with respect. Great care must be used in making decisions about what to purchase and when to purchase. Shopping is a necessary part of my life and though I may certainly enjoy the experience of shopping, I will purchase only those items that I truly need and use. I feel good about this decision and I am able to shop with a new strength and a sense of purpose. When I actually buy something it will be out of needing to use that item. This is my purpose in shopping.

Credit Card Wisdom

I possess the power and the discipline to limit my purchases to those I can afford. I will only buy as much as I can pay for, in full, at that very moment. In this way I am more than able to control my spending. I will rely upon my intelligence and wisdom to make purchasing decisions and I will reject the use of credit cards in making my decisions. Only in the most extreme emergencies will I use a credit card, never on something less important. I feel strong and happy about this, knowing that by relying on my real resources instead of credit cards, I will actually have much, much more in the long run. I feel as though a great weight has been lifted from me.

Controlling Hyperactive Behavior

I can picture myself as a clam, relaxed person. I am able to gather all of my thoughts together and concentrate on whatever I have chosen to do. I am placing all of my attention on just one thing at a time. In this way, I am able to understand more of what people are saying. I am able to understand more of what I am seeing. I am able to understand more of what I read. I can learn more. I can do this any time I want. If I should feel myself becoming too excited, I only have to say this to myself: calm down; pick out the thing I want to do; now put my thinking on that one place. This will work and I will enjoy myself much more.

Exercising Regularly

I have decided that I want to exercise for better health and for enjoyment. I will think carefully about what form of exercise is best for me, seeking the advice of experts. I will look for a safe, useable plan. Then, when I have found a program to fit my needs, I will call on my inner strength and power to follow that program to the best of my ability. If I become discouraged from time to time, I will have the patience and wisdom to return to the plan quickly. I feel great, knowing that I am able to do this. I enjoy the satisfaction of exercising regularly and wisely.

Gambling Control

In the past, I have gambled. I know this has been an incorrect decision. Gambling has hurt me in many ways. Gambling has prevented me from living the wonderful life I deserve. Every person deserves a happy, productive life and so do I. I have a great strength and power within me. I now call upon that inner power which I can feel moving throughout my entire body and mind. I choose to use this power to reject gambling and over things that keep me from my wonderful life. Each time gambling comes forward, I will reject it and send it away. Instead of gambling, I occupy myself with productive, useful activities. If I momentarily slip and want to gamble, I will call on my inner power immediately, wherever I may be. This will bring me back to doing good and useful things. In this way I truly win. I feel good. I feel myself a winner when I reject gambling.

Comfortable Flying

There may come a time when it is necessary for me to fly in an airplane. I have decided to relax and enjoy the experience. I am able and willing to place my trust in the pilot and crew, knowing that they are well-trained professionals who will do their jobs with skill and intelligence. Each one of them wants me to have a safe, good flight. When I feel and hear the engines of the plane, I understand the tremendous power they possess and I know this power is to be used for my safe flight. I can picture myself seated, secure and happy in the plane. I am confident that I will enjoy a wonderful flying experience.

Body Image, Body Shaping

I am a wonderful, capable person with many gifts and good qualities. Whatever my body looks like is secondary to my sense of well-being. I can see myself in the mirror and be happy no matter what I see there. However, if I wish, I can change certain things about my appearance. I do possess a great inner power and strength which I may use to direct my body to change in shape and appearance. If I wish, I can direct my body to grow in certain parts and even decrease in other parts. As I look at myself in the mirror, I can see the parts I want to increase in size. I focus my inner power on these parts and I can see them taking the shape and size I want. I direct my body to move toward this increase in size, day by day, until I am satisfied. I am also able to see another part or parts of my body which I wish to decrease in size. I focus my inner power on this and I can see them taking the shape and size I want. I direct my body to move toward this decrease in size day by day, until I am satisfied.

Being on Time

Inside me, I possess an inner clock which knows the time. Using this clock, I have the ability to follow a schedule and be on time for anything I choose. I can tell myself to wake up at a certain time, and I will. I can judge accurately how much time I will need to get ready for something and I will be ready. In addition to my inner clock, I also have an inner strength which I may direct in any way I choose. I decide to direct my inner strength to cause me to do what is safely necessary to be on time. Having this power feels good to me. I am confident that I will be successfully on time from now on.

Post Traumatic Stress

I have experienced something very unpleasant and stressful. Maybe it has actually caused me some physical injury. Maybe it has actually caused me some emotional injury. Maybe both. Whatever my experience has been, it is now time for me to heal myself both emotionally and physically. Exactly why I have been chosen for this experience is something no human being can accurately answer. It may be that I will never know the precise answer. Understanding that there is no answer to some questions is my only answer. I need to focus my attention and my strength on healing, in order to live the happiest, most rewarding life I can. I possess a wonderful inner strength which I will use to do this. I can direct this strength in any direction I wish. I choose to use my strength for healing and happiness.

Obsessive/Compulsive Control

I sometimes find myself able to think about only one thing. In the past, I have felt that I have no control over this. I may even play out certain rituals in order to try to have some control over this thing I am thinking about. I know that it has kept me from doing and thinking about other, more productive things. It has decreased some of the quality of my life. I am not as happy a person as I could be. I, therefore, now decide to change the way I think about this thing. I understand that whatever has happened in the past, I have an inner power to make my life what I now want it to be. Whatever the result, I am a strong and capable person and I will successfully deal with the thing. Playing out rituals only hurts my chances at really dealing with my life, so I have decided to completely reject them. Instead, I will concentrate my powers on those things which a human being is truly able to accomplish. I can't control the whole world, but I can successfully deal with the worst and best that life has to offer.

While various embodiments of the present invention have been described above, it will be recognized by those skilled in the art that modifications of the present invention may be made without departing from the space of the present invention. Therefore, the limits of the present invention are to be determined in view of the claims which follow.

What is claimed is:

1. An apparatus providing a media with a compute program imprinted thereon operable within an interactive computer device comprising means for presenting to the visual and auditory senses of a user and further comprising means for receiving user-entered information, such information being used by said apparatus to create a customized, user designed hypnosis script which customized script is then presented to the user by said presenting means for the purpose of inducing a state of hypnosis in and making behavioral hypnosis suggestions to said user.

2. A method for inducing a states of hypnosis and heightened level of suggestibility:

a) providing a customizable hypnotic script through the use of a computer program operable within an interactive computer device comprising means for presenting to the visual and auditory senses of a user, further comprising means for receiving user-entered information;

b) querying a user to provide imagery word suggestions for insertion by the program into said script;

c) querying a user to select a behavioral suggestion for insertion by said program into the script; and d) activating said presenting means such that the hypnotic script may be presented to the user to induce a hypnotic state in the user and for providing the user with the user entered and selected behavioral imagery and suggestions.

3. An apparatus providing a media with a computer program imprinted thereon operable within an interactive computer device comprising means for presenting to the visual and auditory senses of a user and further comprising mean to receiving user-entered information, said apparatus being for the purpose of creating a user-designed hypnosis script customized through the use of the user-entered information means which is then presented to the user by said presenting means for the purpose of inducing a state of hypnosis in and making behavioral hypnosis suggestions to said user; wherein the computer program is comprised of:

a) means for providing a customizable hypnosis script;

b) means for querying a user to provide imagery word suggestions for insertion by the program into said script;

c) means for querying a user to select a behavioral suggestion for insertion by said program into the script; and d) means for activating said presenting means such that the hypnotic script may be presented to the user to induce a hypnotic state in the user and for providing the user entered and selected behavioral imagery and suggestions.

* * * * *